US009522236B2

(12) United States Patent
Schneider et al.

(10) Patent No.: US 9,522,236 B2
(45) Date of Patent: *Dec. 20, 2016

(54) DRUG DELIVERY DEVICE AND CARTRIDGE HOLDER FOR A DRUG DELIVERY DEVICE

(71) Applicant: SANOFI-AVENTIS DEUTSCHLAND GMBH, Frankfurt am Main (DE)

(72) Inventors: Christiane Schneider, Frankfurt am Main (DE); Tobias Stever, Frankfurt am Main (DE); Michael Harms, Frankfurt am Main (DE); Ulrik Jakobi, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/666,675

(22) Filed: Mar. 24, 2015

(65) Prior Publication Data
US 2015/0190579 A1 Jul. 9, 2015

Related U.S. Application Data

(63) Continuation of application No. 14/113,860, filed as application No. PCT/EP2012/058182 on May 4, 2012.

(30) Foreign Application Priority Data

May 6, 2011 (EP) ..................................... 11165047

(51) Int. Cl.
*A61M 5/00* (2006.01)
*A61M 5/31* (2006.01)
(Continued)

(52) U.S. Cl.
CPC ............. *A61M 5/3135* (2013.01); *A61M 5/24* (2013.01); *A61M 5/31543* (2013.01);
(Continued)

(58) Field of Classification Search
CPC ..... A61M 5/24; A61M 5/3125; A61M 5/3135
(Continued)

(56) References Cited

U.S. PATENT DOCUMENTS 1,512,294 A * 10/1924 Marcy ..................... A61M 5/24
222/326
2,461,481 A * 2/1949 Roehr ........................... 604/201
6,090,082 A * 7/2000 King et al. .................... 604/234

FOREIGN PATENT DOCUMENTS

EP 1923083 5/2008
WO 93/10839 6/1993
(Continued)

OTHER PUBLICATIONS

International Search Report for Int. App. No. PCT/EP2012/058182, completed Jun. 19, 2012.

*Primary Examiner* — Edelmira Bosques
(74) *Attorney, Agent, or Firm* — McDonnell Boehnen Hulbert & Berghoff LLP

(57) ABSTRACT

A drug delivery device is provided with a cartridge holder having at least one guide track, and a body having at least one interaction member adapted and arranged to mechanically cooperate with the at least one guide track. The guide track has a first section and a second section, wherein the path which is defined by the first section encloses an angle with the longitudinal axis of the device, wherein the angle which is enclosed by the path defined by the first section with the longitudinal axis is smaller than the angle which is enclosed by the path defined by the second section with the longitudinal axis.

14 Claims, 5 Drawing Sheets

(51) Int. Cl.
*A61M 5/24* (2006.01)
*A61M 5/315* (2006.01)

(52) U.S. Cl.
CPC .... *A61M 5/31551* (2013.01); *A61M 5/31585* (2013.01); *A61M 5/31535* (2013.01); *A61M 5/31541* (2013.01); *A61M 5/31575* (2013.01); *A61M 2005/2407* (2013.01); *A61M 2005/2477* (2013.01); *A61M 2005/2488* (2013.01); *A61M 2205/581* (2013.01); *A61M 2205/582* (2013.01); *A61M 2205/6045* (2013.01)

(58) Field of Classification Search
USPC ........................................................ 604/187
See application file for complete search history.

(56) References Cited

FOREIGN PATENT DOCUMENTS

| WO | 2008/000827 | 1/2008 |
|----|-------------|--------|
| WO | 2008/059063 | 5/2008 |
| WO | 2008/062025 | 5/2008 |

* cited by examiner

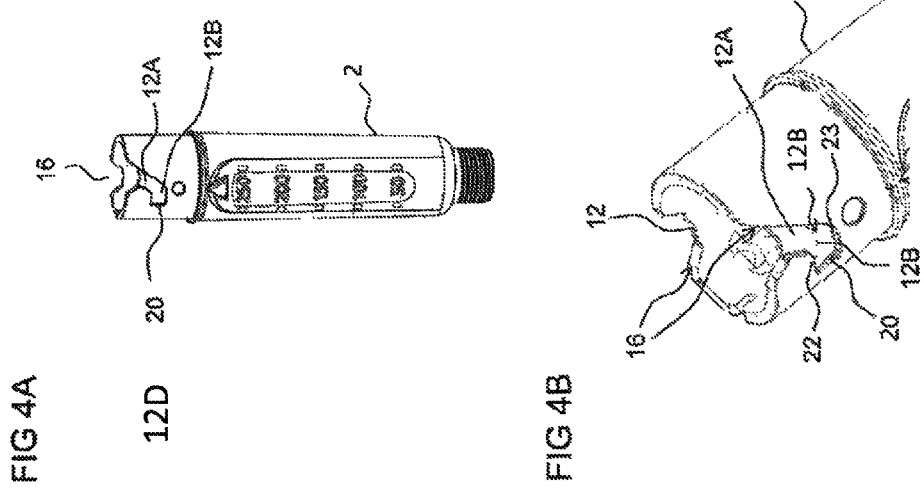

DRUG DELIVERY DEVICE AND CARTRIDGE HOLDER FOR A DRUG DELIVERY DEVICE

CROSS REFERENCE TO RELATED APPLICATIONS

The present application is a continuation of U.S. patent application Ser. No. 14/113,860, filed Oct. 25, 2013, which is a U.S. National Phase Application pursuant to 35 U.S.C. §371 of International Application No. PCT/EP2012/058182 filed May 4, 2012, which claims priority to European Patent Application No. 11165047.9 filed May 6, 2011. The entire disclosure contents of these applications are herewith incorporated by reference into the present application.

FIELD OF DISCLOSURE

This disclosure relates to a drug delivery device. The disclosure further relates to a cartridge holder for a drug delivery device.

BACKGROUND

In a drug delivery device, often, a bung within a cartridge containing a plurality of doses of a drug is displaced by a piston rod. Thereby, a dose of the drug is expelled from the cartridge. The cartridge is often stabilized by a cartridge holder.

A drug delivery device is described in document EP 1 923 083 A1, for example.

SUMMARY

It is an object of the present disclosure to provide an improved drug delivery device, for example a device with increased comfort for the user. Furthermore, a cartridge holder is provided facilitating provision of an improved drug delivery device.

This object may be achieved by the subject matter of the independent claims. Advantageous embodiments and refinements are subject matter of the dependent claims.

One aspect relates to a drug delivery device. The device may comprise a cartridge holder. The cartridge holder may comprise at least one, preferably two or more, guide tracks. The device may comprise a body. The body may comprise at least one, preferably two or more, interaction members. The interaction member may be adapted and arranged to mechanically cooperate with the at least one guide track. The guide track expediently comprises a first section and a second section. The first section may run obliquely with respect to the longitudinal axis of the device. In particular, the path which is defined by the first section encloses an angle with the longitudinal axis of the device. The second section may run less obliquely with respect to the longitudinal axis of the device than the first section. In particular, the angle which is enclosed by the path defined by the first section with the longitudinal axis of the device may be smaller than the angle which is enclosed by the path defined by the second section with the longitudinal axis of the device. The second section may run transversally with respect to the longitudinal axis of the device. For, preferably releasably, connecting the cartridge holder to the body, the interaction member may be configured to mechanically cooperate with the first section such that the cartridge holder is axially moved and rotated with respect to the body. Furthermore, for preferably releasably, connecting the cartridge holder to the body, the interaction member may be configured to mechanically cooperate with the second section such that the cartridge holder is rotated with respect to the body. Thereby, axial movement of the cartridge holder with respect to the body may be prevented.

When the interaction member mechanically cooperates with the guide track, the cartridge holder performs an inter alia rotatory movement. In particular, the rotatory movement is performed already when the cartridge holder is moved towards the body for connecting the cartridge holder to the body, i.e. when the interaction member mechanically cooperates with the first section. The rotatory movement is a movement very familiar to the user as it is known from ordinary screw thread connections. Thus, the user can feel very familiar with the connecting movement. In particular, this connecting movement of the cartridge holder may help in that the user can easily trust in the safe connection of the cartridge holder and the body. In this way, provision of a device comprising increased user comfort is facilitated.

Mechanical cooperation of the interaction member and the first section may be succeeded by mechanical cooperation of the interaction member and the second section for connecting the cartridge holder and the body. Axial movement of the cartridge holder with respect to the body may be prevented when the interaction member mechanically cooperates with the second section. This may help to indicate to the user that the cartridge holder is close to a final position with respect to the body, in particular to a position where the cartridge holder is firmly connected to the body. User comfort may be further increased in this way.

The interaction member and the first and second section may comprise a dimension such that the interaction member abuts the walls of the respective section any time during the connection operation. In particular, the interaction member may exactly fit into the respective section. In this way, a smooth connection movement of the cartridge holder may be facilitated which further helps to increase the user comfort.

According to an embodiment, the cartridge holder is rotated only in a first direction with respect to the body during mechanical cooperation of the interaction member with the first and second section.

Accordingly, during the connection operation, the cartridge holder may be rotated in the same direction. No opposite rotation, in particular no change of the rotation direction, of the cartridge holder may be necessary for connecting the cartridge holder to the body, which could lead to the user erroneously believing that the cartridge holder is not safely connected to the body or even released from the body.

According to an embodiment, the second section comprises an angular end stop. The angular end stop may comprise a sidewall of the second section. The angular end stop may be adapted and arranged to prevent further relative rotation of the cartridge holder and the body in the first direction by mechanical cooperation of the angular end stop with the interaction member.

The angular end stop may be configured for indicating the final position of the cartridge holder with respect to the body. Hence, when the user can no longer rotate the cartridge holder in the first direction with respect to the body, he automatically knows that the cartridge holder was firmly connected to the body. User comfort may be further increased in this way.

According to an embodiment, the cartridge holder is rotated with respect to the body by less than one revolution when the interaction member mechanically cooperates with the first section. The cartridge holder may be rotated with respect to the body by less than one revolution when the interaction member mechanically cooperates with the second section.

The cartridge holder may be rotated by a minimum angle of 5 degrees when the interaction member mechanically cooperates with the first section. The cartridge holder may be rotated by a maximum angle of 120 degrees when the interaction member mechanically cooperates with the first section. The cartridge holder may be rotated by an angle between 10 degrees and 50 degrees, for example. Preferably, the cartridge holder is rotated by an angle of 30 degrees when the interaction member mechanically cooperates with the first section.

The cartridge holder may be rotated by a minimum angle of 5 degrees when the interaction member mechanically cooperates with the second section. The cartridge holder may be rotated by a maximum angle of 90 degrees when the interaction member mechanically cooperates with the second section. The cartridge holder may be rotated by an angle between 10 and 20 degrees, for example, when the interaction member mechanically cooperates with the second section. Preferably, the cartridge holder is rotated by an angle of 15 degrees, when the interaction member mechanically cooperates with the second section.

Rotating the cartridge holder by less than one revolution during the connection operation may further help to increase the user comfort, as the user only has to perform small and, thus, easily manageable movements of the cartridge holder for safely connecting the cartridge holder to the body.

According to an embodiment, the cartridge holder is rotated by a greater angle with respect to the body when the interaction member mechanically cooperates with the first section than when the interaction member mechanically cooperates with the second section.

According to an embodiment, the cartridge holder is rotated by a greater angle with respect to the body when the interaction member mechanically cooperates with the second section than when the interaction member mechanically cooperates with the first section.

According to an embodiment, the cartridge holder is rotated by the equal angle with respect to the body when the interaction member mechanically cooperates with the second section and when the interaction member mechanically cooperates with the first section.

According to an embodiment, for disconnecting the cartridge holder and the body, the interaction member is configured to mechanically cooperate with the second section and with the first section of the guide track such that the cartridge holder is rotated in a second direction with respect to the body. The second direction may be opposite to the first direction.

Mechanical cooperation of the interaction member and the second section may be succeeded by mechanical cooperation of the interaction member and the first section for disconnecting the cartridge holder and the body. For disconnecting the cartridge holder and the body, a reverse movement of the cartridge holder may be required as compared to the connecting movement. No additional disconnecting movements may be required. In this way, provision of a drug delivery device providing increased user comfort may be facilitated.

According to an embodiment, the guide track comprises a groove. The at least one guide track may be arranged on an outer surface of the cartridge holder. Alternatively, the guide track may be arranged on the body, e.g. on an inner surface of the body. The interaction member may comprise a protrusion or pin. The at least one interaction member may be arranged on an inner surface of the body. Alternatively, the interaction member may be arranged on the cartridge holder, e.g. on an outer surface of the cartridge holder.

According to an embodiment, the guide track is arranged in the proximal end section of the cartridge holder. The proximal end section may comprise at least one indentation. The guide track may be arranged such that the distal end of the indentation passes over into the proximal end of the first section of the guide track.

The indentation may comprise an angular extent which is greater than the angular extent of the first section. The indentation may comprise a sloped edge which is configured to facilitate introducing the interaction member into the indentation. By providing the indentation in the proximal end section, the interaction member may be easily guideable into the first section of the guide track once introduced in the indentation.

According to an embodiment, the first section and the second section of the guide track pass over into one another.

In this way, a continuous rotatory movement of the cartridge holder, in particular a rotation of the cartridge holder without abrupt movements or interruptions, may be enabled when the cartridge holder is connected to the device.

According to an embodiment, the cartridge holder may comprise two different guide tracks. The guide tracks may be arranged oppositely with respect to one another. The body may comprise two interaction members. The interaction members may be arranged oppositely with respect to one another.

By providing two guide tracks and two interaction members a safe and easily manageable connection of the cartridge holder and the body may be enabled.

A further aspect relates to a cartridge holder for a drug delivery device. The cartridge holder may comprise the previously described cartridge holder. The cartridge holder may comprise at least one guide track. The guide track may comprise a first section. The first section may run obliquely with respect to the longitudinal axis of the cartridge holder. The guide track may comprise a second section. The second section may run less obliquely with respect to the longitudinal axis of the cartridge holder than the first section. The second section may run transversally with respect to the longitudinal axis of the cartridge holder.

The path which is defined by the first section may enclose an angle with the longitudinal axis of the cartridge holder. The angle which is enclosed by the path defined by the first section with the longitudinal axis may be smaller than the angle which is enclosed by the path defined by the second section with the longitudinal axis.

The guide track may enable a continuous rotatory movement of the cartridge holder, in particular a rotation without abrupt movements or interruptions, when the cartridge holder is connected to the device. The rotatory movement may be performed already when the cartridge holder is moved towards the device. Such a rotatory movement is known from ordinary screw thread connections and, thus, it is very familiar to the user. Accordingly, the connecting movement of the cartridge holder may help in that the user can easily trust in the safe connection of the cartridge holder and the device. In this way, provision of a device comprising increased user comfort is facilitated.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

Like elements, elements of the same kind and identically acting elements may be provided with the same reference numerals in the figures.

DETAILED DESCRIPTION

Figure 1:
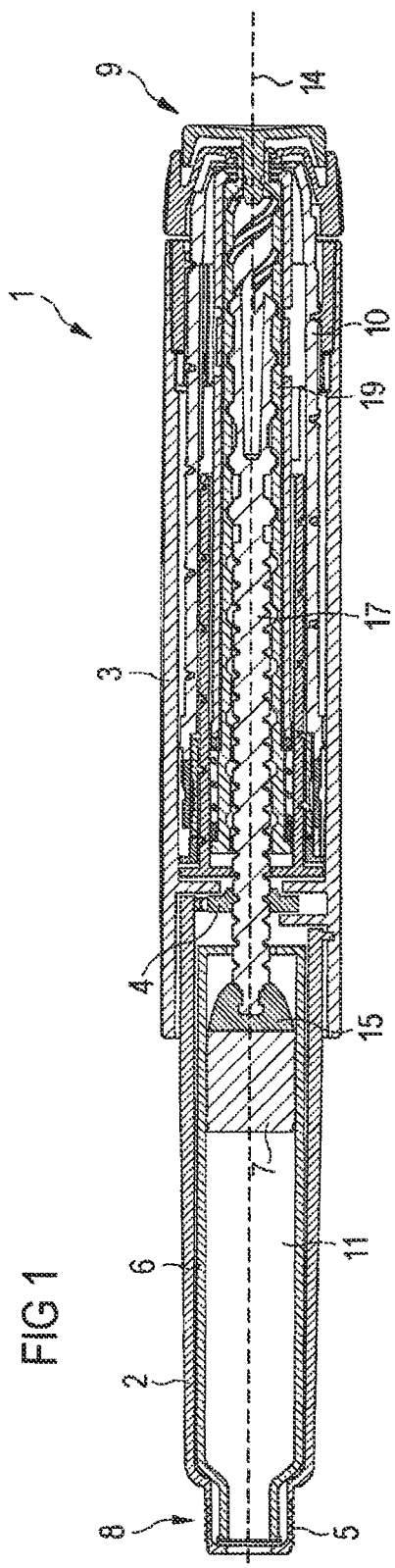
FIG. 1 schematically shows a sectional side view of a drug delivery device.
Figure 2A:
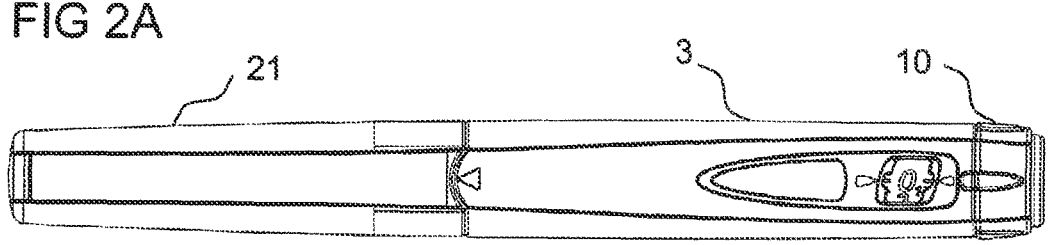
FIGS. 2A and 2B schematically show a perspective side view of the drug delivery device of FIG. 1, FIG. 3 schematically shows a perspective side view of a body, FIGS. 4A-4D schematically show a perspective side view of a cartridge holder.
Figure 2B:
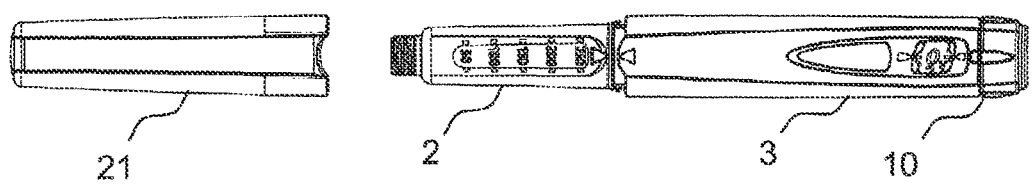

In FIGS. 1, 2A and 2B a drug delivery device 1 is shown. The drug delivery device 1 comprises a body 3. The drug delivery device 1 and the body 3 have a distal end and a proximal end. The distal end is indicated by arrow 8. The proximal end is indicated by arrow 9. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis 14 of the device 1 (see FIG. 1).

The drug delivery device 1 comprises a cartridge holder 2. The cartridge holder 2 comprises engaging means 5, e.g. a thread, for releasably connecting a needle assembly (not explicitly shown) to the cartridge holder 2. A cap 21 (see FIGS. 2A and 2B) can be secured to the drug delivery device 1 for protecting the device 1, and, in particular, the cartridge holder 2 from environmental influences.

The drug delivery device 1 comprises a cartridge 6. The cartridge 6 is retained within the cartridge holder 2. The cartridge holder 2 stabilizes the position of the cartridge 6 mechanically. The cartridge 6 contains a drug 11, preferably a plurality of doses of the drug 11.

The drug 11 may be a fluid drug. The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4derivative;
or an Exendin-4derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38, [Asp28] Exendin-4 (1-39)-NH2,
des Pro36, Pro37, Pro38, [Asp28] Exendin-4(1-39)-(Lys)6-NH2,
H-(Lys)6-des Pro36, Pro37, Pro38, [Asp28] Exendin-4(1-39)-(Lys)6-NH2,
H-Asn-(Glu)5-des Pro36, Pro37, Pro38, [Asp28] Exendin-4(1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38, [Trp(O2)25] Exendin-4 (1-39)-NH2, H-(Lys)6-des Pro36, Pro37, Pro38, [Trp(O2)25, Asp28] Exendin-4(1-39)-NH2, H-Asn-(Glu)5-des Pro36, Pro37, Pro38, [Trp(O2)25, Asp28] Exendin-4(1-39)-NH2, des Pro36, Pro37, Pro38, [Trp(O2)25, Asp28] Exendin-4(1-39)-(Lys)6-NH2, H-(Lys)6-des Pro36, Pro37, Pro38, [Trp(O2)25, Asp28] Exendin-4(1-39)-(Lys)6-NH2, H-Asn-(Glu)5-des Pro36, Pro37, Pro38, [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38, Exendin-4(1-39)-NH2, H-(Lys)6-desPro36, Pro37, Pro38, [Met(O)14, Asp28] Exendin-4(1-39)-NH2, H-Asn-(Glu)5-des Pro36, Pro37, Pro38, [Met(O)14, Asp28] Exendin-4(1-39)-NH2, des Pro36, Pro37, Pro38, [Met(O)14, Asp28] Exendin-4(1-39)-(Lys)6-NH2, H-(Lys)6-des Pro36, Pro37, Pro38, [Met(O)14, Asp28] Exendin-4(1-39)-(Lys)6-NH2, H-Asn-(Glu)5 des Pro36, Pro37, Pro38, [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38, [Met(O)14, Trp(O2)25] Exendin-4(1-39)-NH2, H-(Lys)6-des Pro36, Pro37, Pro38, [Met(O)14, Asp28] Exendin-4(1-39)-NH2, H-Asn-(Glu)5-des Pro36, Pro37, Pro38, [Met(O)14, Trp(O2)25, Asp28] Exendin-4(1-39)-NH2, des Pro36, Pro37, Pro38, [Met(O)14, Trp(O2)25, Asp28] Exendin-4(1-39)-(Lys)6-NH2, H-(Lys)6-des Pro36, Pro37, Pro38, [Met(O)14, Trp(O2)25, Asp28] Exendin-4(S1-39)-(Lys)6-NH2, H-Asn-(Glu)5-des Pro36, Pro37, Pro38, [Met(O)14, Trp(O2)25, Asp28] Exendin-4(1-39)-(Lys)6-NH2;

or a pharmaceutically acceptable salt or solvate of any one of the afore-mentioned Exedin-4derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich", shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment", contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences"17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 1 may be a pen-type device, in particular a pen-type injector. The device 1 may be configured for dispensing fixed doses of the drug 11, i.e. doses which may not be varied by a user, or user-settable doses of the drug 11. A bung 7 is slideably retained within the cartridge 6. The bung 7 seals the cartridge 6 proximally. Movement of the bung 7 in the distal direction with respect to the cartridge 6 causes the drug 11 to be dispensed from the cartridge 6.

The body 3 houses a drive mechanism 4, 10, 19 of the device 1. The drive mechanism 4, 10, 19 drives a piston rod 17 in the distal direction with respect to the body 3 for dispensing a dose of the drug 11. The drive mechanism 4, 10, 19 prevents proximal movement of the piston rod 17 with respect to the body 3 during a dose setting operation. A bearing member 15 is located at the distal end of the piston rod 17 to abut the proximal face of the bung 7.

Figure 3:
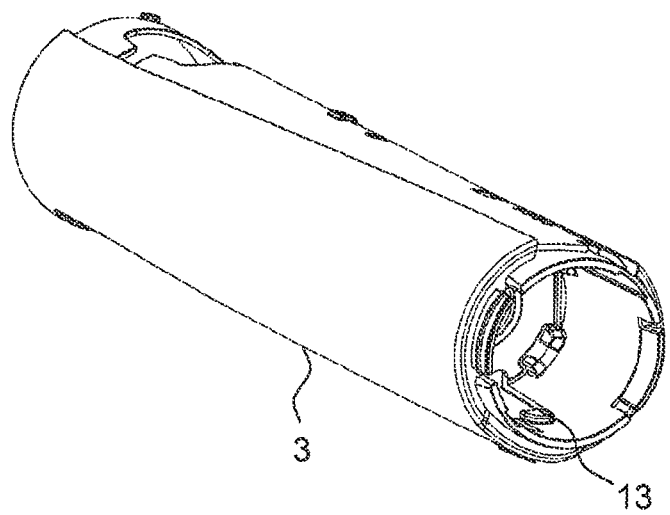

FIG. 3 schematically shows a perspective side view of a body 3.

The cartridge holder 2 is releasably connected to the body 3 of the drug delivery device 1. The body 3 comprises two interaction members 13, wherein only one of the interaction members 13 is shown in FIG. 3. Alternatively, the body 3 can comprise only one interaction member 13 or even more, e.g. three or four interaction members 13.

The interaction members 13 are arranged in the distal end section of the body 3, i.e. the end section which is to be connected to the cartridge holder 2. The interaction members 13 are arranged on the inner surface of the body 3. The two interaction members 13 are arranged oppositely with respect to one another.

The interaction member 13 comprises a pin. The pin protrudes radially inwards from the inner surface of the body 3. In the embodiment shown in FIG. 3, the angular extent of the interaction member 13 is greater than its axial extent. However, the situation may be vice versa, as well, i.e. the axial extent of the interaction member 13 may be greater than its angular extent. Alternatively, the interaction member 13 can comprise a square or circular shape. The respective interaction member 13 mechanically cooperates with a corresponding guide track 12 of the cartridge holder 2.

Figure 4C:
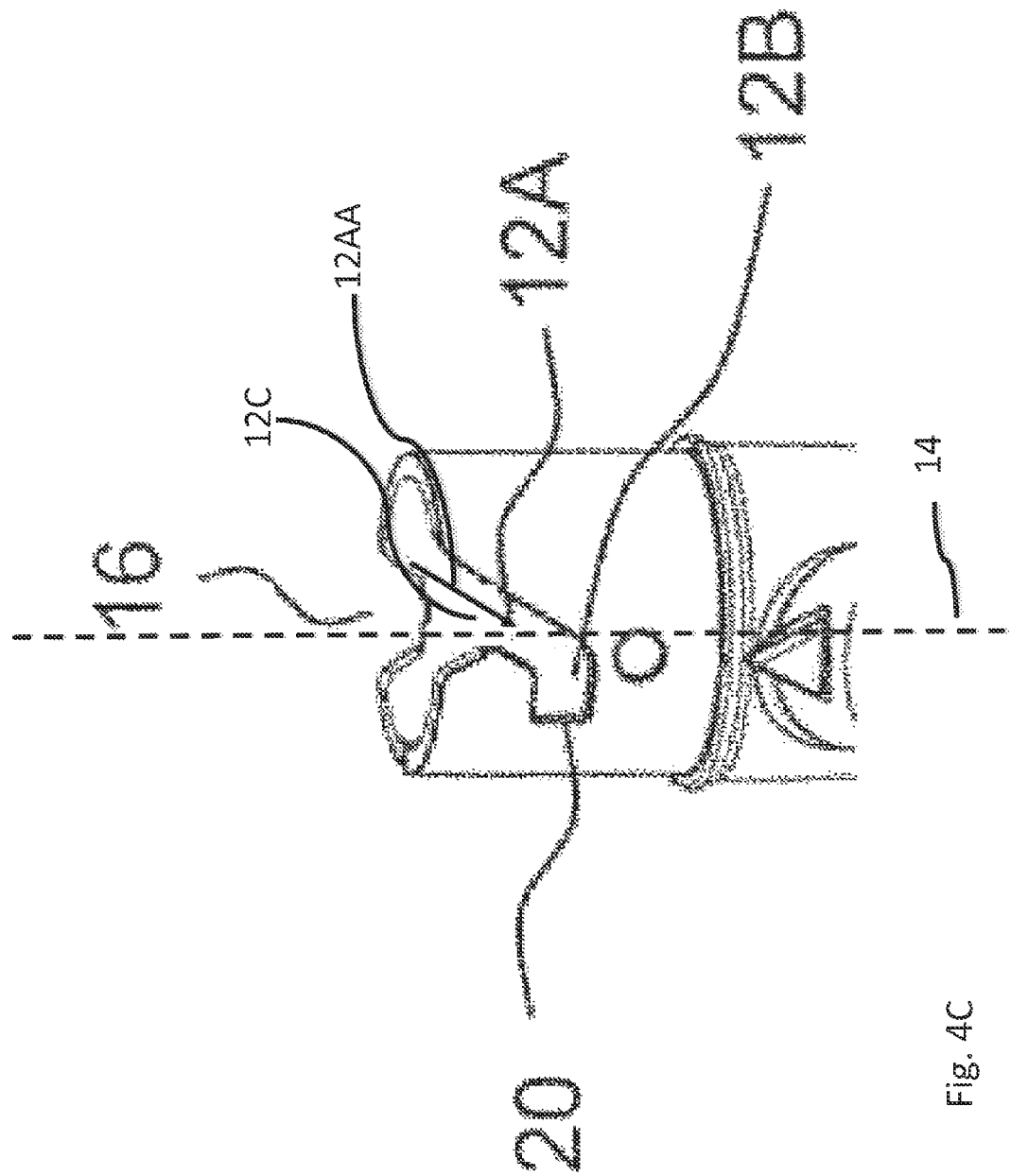
Figure 4D:
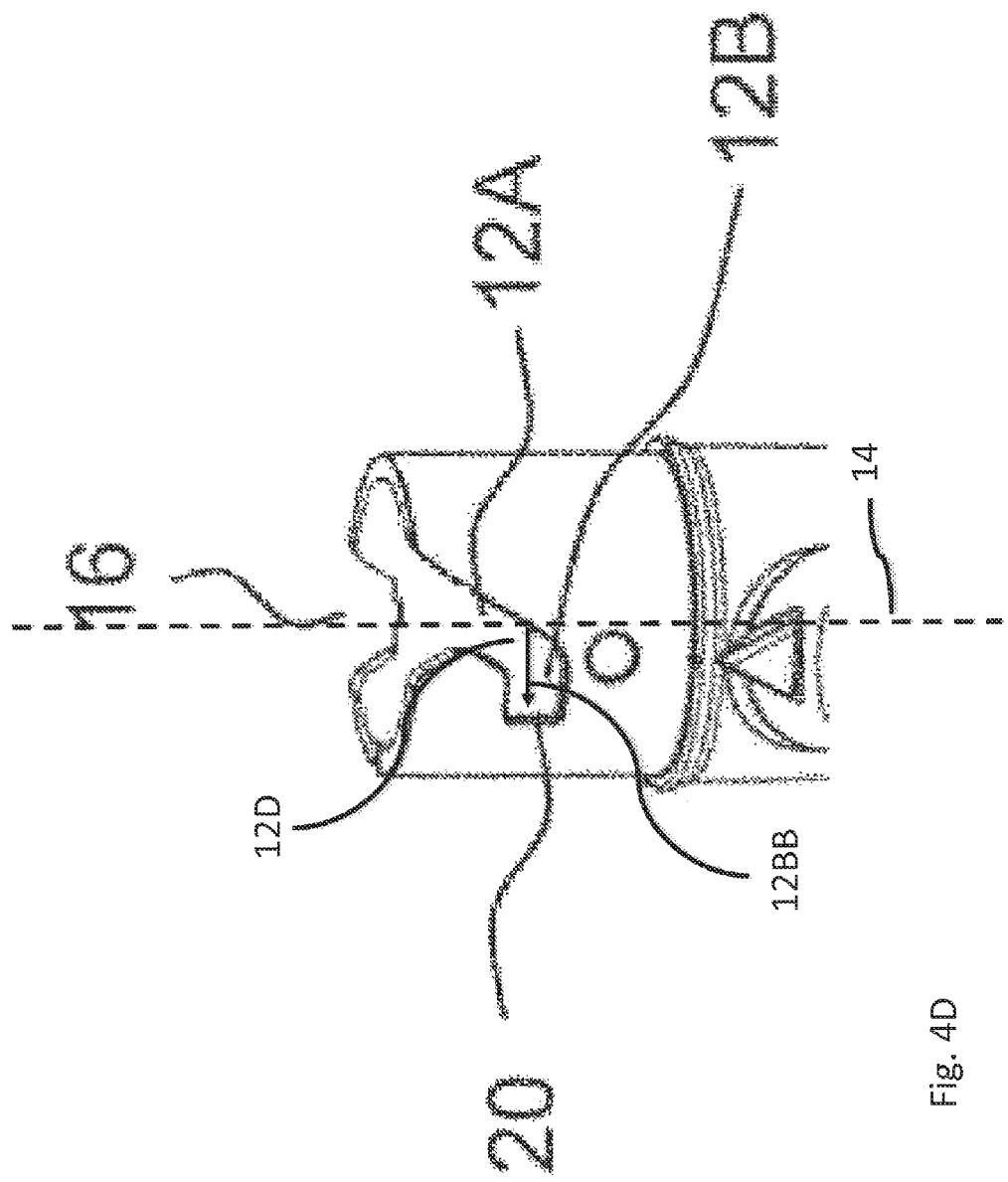

FIGS. 4A and 4B schematically show a perspective side view of the cartridge holder 2.

The cartridge holder 2 comprises two guide tracks 12. Alternatively, the cartridge holder 2 can comprise only one guide track 12 or even more, e.g. three or four guide tracks 12. The number of guide tracks 12 corresponds to the number of interaction members 13. The guide tracks 12 are arranged in the proximal end section of the cartridge holder 2, i.e. the end section which is to be connected to the body 3. The guide tracks 12 are arranged on the outer surface of the cartridge holder 2. The guide tracks 12 are grooves. The two guide tracks 12 are arranged oppositely with respect to one another.

The respective guide track 12 (see FIG. 4B) comprises a first section 12A. The guide track 12 comprises a second section 12B. The first section 12A runs obliquely with respect to the longitudinal axis 14 (see FIG. 1) of the device 1. In particular, the path 12AA defined by the first section 12A encloses an angle 12C with the longitudinal axis 14 of the device 1. The angle 12C which is enclosed by the path 12AA defined by the first section 12A with the longitudinal axis 14 amounts to about 45 degrees in the embodiment shown in FIGS. 4A 4B, 4C and 4D. However, also other angles are conceivable, e.g. the angle can amount to a minimum value of 10 degrees or a maximum value of 120 degrees. The second section 12B runs less obliquely with respect to the longitudinal axis 14 than the first section 12A. The angle 12C enclosed by the path 12AA defined by the first section 12A with the longitudinal axis 14 is smaller than the angle 12D enclosed by the path 12BB defined by the second section 12B with the longitudinal axis 14. The angle which is enclosed by the path defined by the second section 12B with the longitudinal axis 14 amounts to 90 degrees in the embodiments shown in FIGS. 4A and 4B.

The first section 12A and the second section 12B form a continuous guide track 12. In other words, for connecting or disconnecting the cartridge holder 2 to the body 3, the interaction member 13 can pass from the first section 12A directly into the second section 12B and vice versa.

The second section 12B comprises an angular stop face 20. The angular stop face 20 is formed by a sidewall of the second section 12B. When the interaction member 13 mechanically cooperates with the angular stop face 20, further rotation of the cartridge holder 2 with respect to the body 3 for connecting the cartridge holder 2 and the body 3 is prevented.

The cartridge holder 2 further comprises two indentations 16. The indentations 16 are arranged in the proximal end section of the cartridge holder 2. The two indentations 16 are arranged oppositely with respect to one another. The respective indentation 16 comprises sloped edges. The indentation 16 comprises an angular extent which is greater than the angular extent of the first section 12A. Alternatively, the indentation 16 may comprise an angular extent which is smaller than the angular extend of the first section 12A. The distal end of the respective indentation 16 passes over into the proximal end of the first section 12A of the respective guide track 12.

For connecting the cartridge holder 2 to the body 3, the cartridge holder 2 is moved, in particular at least one of axially moved and rotated, with respect to the body 3. The cartridge holder 2 is moved with respect to the body 3 until the interaction member 13 mechanically cooperates with the indentation 16. Upon further movement of the cartridge holder 2 with respect to the body 3, the interaction member is brought into mechanical cooperation with the first section 12A. When the interaction member 13 mechanically cooperates with the first section 12A, the cartridge holder 2 is moved proximally with respect to the body 3 such that the first section 12A slides along the interaction member 13. Thereby, the cartridge holder 2 is rotated in a first direction with respect to the body 3. In this embodiment, the cartridge holder 2 is rotated by an angle of about 30 degrees with respect to the body while the interaction member 13 mechanically cooperates with the first section 12A. The angle is defined by the angle which the path defined by the first section 12A encloses with the longitudinal axis 14 as described above.

At the distal end of the first section 12A, the first section 12A directly passes over into the second section 12B. At the distal end of the first section 12A, the interaction member 13 is brought into mechanical cooperation with a distal and a proximal wall 22, 23 (see FIG. 4B) of the second section 12B such that further axial movement of the cartridge holder 2 with respect to the body 3 is prevented. In particular, mechanical cooperation of the interaction member 13 with the distal wall 23 prevents further proximal movement of the cartridge holder 2 with respect to the body 3 during the connection operation.

Accordingly, the cartridge holder 2 is further rotated in the first direction, but no longer axially moved with respect to the body 3. The cartridge holder 2 is rotated such that the second section 12B slides along the interaction member 13 until the interaction member 13 mechanically cooperates with the angular end stop 20. The cartridge holder 2 is rotated in the same direction when the interaction member 13 mechanically cooperates with the first and the second section 12A, 12B for connecting the cartridge holder 2 to the body 3.

When the interaction member 13 mechanically cooperates with the angular end stop 20, further rotation of the cartridge holder 2 in the first direction is prevented. When the interaction member 13 mechanically cooperates with the angular end stop 20, the cartridge holder 2 is firmly connected to the body 3. Mechanical cooperation of the interaction member 13 and the angular end stop 20 can provide a tactile feedback indicating to the user that the cartridge holder 2 is firmly connected to the body 3.

For disconnecting the cartridge holder 2 and the body 3, the cartridge holder 2 is rotated in a second direction. The second direction is opposite to the first direction. Thereby, the second section 12B slides along the interaction member 13 of the body 3, axial movement of the cartridge holder 2 with respect to the body 3 being prevented by mechanical cooperation of the interaction member 13 with the distal and proximal walls 22, 23 of the second section 12B.

Upon further rotation of the cartridge holder 2 in the second direction, the first section 12A slides along the interaction member 13. When the first section 12A slides along the interaction member 13, the cartridge holder 2 is moved distally with respect to the body 3 for disconnecting the cartridge holder 2 and the body 3.

The interaction member 13 as well as the first section 12A and the second section 12B comprise a dimension such that the interaction member 13 mechanically cooperates with the walls of the sections 12A, 12B at any time during the connecting and during the disconnection operation. In particular, when the interaction member 13 mechanically cooperates with the first section, the interaction member 13 abuts the side walls of the first section 12A. When the interaction member 13 mechanically cooperates with the second section, it abuts the distal and proximal walls 22, 23 of the second section 12B. As the first and second section 12A, 12B pass over into one another, i.e. the side walls of the first section 12A pass over into the distal and proximal walls 22, 23 of the second section 12B, the interaction member 13 is at any time in mechanical contact with the wall of one of the sections 12A, 12B during the connection and the disconnection operation.

The invention claimed is:

1. A drug delivery device comprising
a cartridge holder comprising,
at least two guide tracks located at a proximal end of the cartridge holder, each guide track having the same configuration,
a longitudinal axis
a distal end configured to releasably engage a needle assembly, wherein the cartridge holder has an interior space between the proximal end and the distal end having a length that extends beyond a proximal end of a cartridge containing a plurality of doses of a drug and where the interior space retains and stabilizes the cartridge,
a body having an inner surface housing a drive mechanism, the inner surface comprising at least two protrusions each that mechanically cooperate with the guide tracks such that the proximal end of the cartridge holder is fixedly attached to a distal end of the body such that a bung in the cartridge will abut a piston rod in the drive mechanism,
wherein each guide track comprises a first section and a second section, wherein the first section defines a first path, wherein the first path is orientated and positioned at a first angle relative to the longitudinal axis of the cartridge holder, wherein the second section defines a second path, wherein the second path is orientated and positioned at a second angle relative to the longitudinal axis, wherein the first angle is smaller than the second angle and the first section is located closer to the proximal end of the cartridge holder than the second section,
wherein, for connecting the cartridge holder to the body, the protrusions are configured to mechanically cooperate with the first section such that the cartridge holder can move axially with respect to the body, and the protrusions are further configured to mechanically cooperate with the second section such that the cartridge holder is rotated with respect to the body, whereby an axial movement of the cartridge holder with respect to the body is prevented when the protrusions are cooperating with the second section.

2. The drug delivery device according to claim 1, wherein the cartridge holder is rotated in a first direction with respect to the body during mechanical cooperation of the protrusions with the first and second section.

3. The drug delivery device of claim 2 where the rotation of the cartridge holder in the first direction is less than one revolution during a connection operation.

4. The drug delivery device according to claim 2, wherein the second section comprises an end stop adapted and arranged to prevent further relative rotation of the cartridge holder and the body in the first direction by mechanical cooperation of the end stop with the protrusions.

5. The drug delivery device according to claim 4, wherein the end stop is configured to automatically indicate to a user that a final position is reached between the cartridge holder and the body.

6. The drug delivery device according to claim 1, wherein the cartridge holder is rotated with respect to the body by less than one revolution when the interaction member mechanically cooperates with the first section, and wherein the cartridge holder is rotated with respect to the body by less than one revolution when the interaction member mechanically cooperates with the second section.

7. The drug delivery device according to claim 2, wherein, for disconnecting the cartridge holder and the body, the protrusions are configured to mechanically cooperate with the second section and then with the first section of the guide tracks such that the cartridge holder is rotated in a second direction with respect to the body, the second direction being opposite to the first direction.

8. The drug delivery device according to claim 1, wherein the first section and the second section of the guide track pass over into one another.

9. The drug delivery device according to claim 1, wherein the guide tracks are arranged on an outer surface of a proximal end of the cartridge holder.

10. The drug delivery device according to claim 1, wherein the guide tracks comprise a groove.

11. The drug delivery device according to claim 1, wherein the cartridge holder comprises three identical guide tracks being arranged equally spaced with respect to one another, and wherein the body comprises three identical protrusions, the protrusions being arranged with respect to one another at a spacing equally to the spacing between the guide tracks.

12. The drug delivery device according to claim 1, wherein the guide tracks are dimensioned such that the protrusions abuts one or more wall s of the first and second sections during a connection operation.

13. The drug delivery device according to claim 1 wherein the cartridge holder is rotated in a first direction when the protrusions mechanically cooperate with the first section and the cartridge holder is rotated in the same, first direction, when the protrusions mechanically cooperate with the second section.

14. The drug delivery device according to claim 1 wherein the first angle is at least 10 degrees.

* * * * *